(12) United States Patent
Baumfalk et al.

(10) Patent No.: US 8,859,949 B2
(45) Date of Patent: Oct. 14, 2014

(54) SENSOR DEVICE, COMPRISING AN OPTICAL SENSOR, A CONTAINER AND A COMPARTMENTALIZATION MEANS

(75) Inventors: Reinhard Baumfalk, Goettingen (DE); Stefan Weisshaar, Adelebsen (DE); Gerhard Greller, Goettingen (DE); Daniel Riechers, Hannover (DE); Julia Lueders, Lahstedt (DE); Peter Polossek, Bodenfelde OT Amelieth (DE)

(73) Assignee: Sartorius Stedim Biotech GmbH, Goettingen (DE)

( * ) Notice: Subject to any disclaimer, the term of this patent is extended or adjusted under 35 U.S.C. 154(b) by 290 days.

(21) Appl. No.: 13/377,845

(22) PCT Filed: May 22, 2010

(86) PCT No.: PCT/EP2010/003158
§ 371 (c)(1),
(2), (4) Date: Dec. 14, 2011

(87) PCT Pub. No.: WO2010/145747
PCT Pub. Date: Dec. 23, 2010

(65) Prior Publication Data
US 2012/0091326 A1 Apr. 19, 2012

(30) Foreign Application Priority Data

Jun. 19, 2009 (DE) .......................... 10 2009 025 520
Oct. 23, 2009 (DE) .......................... 10 2009 050 448

(51) Int. Cl.
*H01J 5/02* (2006.01)
*A61L 2/28* (2006.01)
(Continued)

(52) U.S. Cl.
CPC . *A61L 2/28* (2013.01); *G01N 21/90* (2013.01);
*A61L 2/081* (2013.01); *G01N 21/80* (2013.01);
*G01N 2021/7786* (2013.01)
USPC ...... 250/239; 250/573; 250/492.1; 435/289.1

(58) Field of Classification Search
CPC ....... G01N 21/01; G01N 21/85; G01N 21/90;
G01N 21/9009; G01N 33/50
USPC .......... 250/239, 216, 573, 576, 492.1, 361 R;
435/289.1
See application file for complete search history.

(56) References Cited

U.S. PATENT DOCUMENTS 6,653,148 B2  11/2003  Trapp et al.
(Continued)

FOREIGN PATENT DOCUMENTS

DE  100 51 220  4/2002
(Continued)

OTHER PUBLICATIONS

Gopala Rao G and Narayana Rao V: "Ascorbic Acid as a reducing agent in quantitive analysis"—Fresenius Journal of Analytical Chemistry—vol. 147, No. 5, Sep. 1, 1955, pp. 338-347.
(Continued)

*Primary Examiner* — Kevin Pyo
(74) *Attorney, Agent, or Firm* — Gerald E. Hespos; Michael J. Porco; Matthew T. Hespos

(57) ABSTRACT

A sensor device has an optical sensor (1), a container (2) and a compartmentalizer (3) that temporarily divides the container into a main space (4) and an adjacent space (5), in which the optical sensor (1) is located. The gas volume in the direct vicinity of the optical sensor (1) is reduced, as are also, consequently, the reactive products generated by radiation sterilization. The adjacent space (5) can be united with the main space (4) after the sterilization as a result of the temporary compartmentalization. The optical sensor is suitable for implementation in containers and laboratory products, such as, for example, disposable bioreactors, that are sterilized by gamma radiation.

12 Claims, 5 Drawing Sheets

(51) Int. Cl.
*G01N 21/90* (2006.01)
*G01N 21/80* (2006.01)
*A61L 2/08* (2006.01)
*G01N 21/77* (2006.01)

(56) References Cited

U.S. PATENT DOCUMENTS

| | | |
|---|---|---|
| 7,390,462 B2 | 6/2008 | Rao et al. |
| 2009/0075362 A1 | 3/2009 | Baumfalk et al. |
| 2011/0266449 A1 | 11/2011 | Wuenn et al. |
| 2012/0267518 A1* | 10/2012 | Weisshaar et al. ............ 250/239 |

FOREIGN PATENT DOCUMENTS

| | | |
|---|---|---|
| DE | 20 2007 005 399 | 8/2007 |
| DE | 10 2009 003 971 | 7/2010 |
| EP | 0 351 516 | 1/1990 |
| EP | 2 065 701 | 6/2009 |
| WO | 02/056023 | 7/2002 |
| WO | 2005/118771 | 12/2005 |

OTHER PUBLICATIONS

International Preliminary Report. PCT/EP2010/003158, 2010.

* cited by examiner

SENSOR DEVICE, COMPRISING AN OPTICAL SENSOR, A CONTAINER AND A COMPARTMENTALIZATION MEANS

BACKGROUND OF THE INVENTION

1. Field of the Invention

The invention relates to a sensor device, having at least one optical sensor, a container and a compartmentalization means.

2. Description of the Related Art

In medical technology and biotechnology, optical sensors are used, in particular, in disposable reactors, mixing reactors and bioreactors or in disposable containers, mixing containers and biocontainers. In these and similar fields of application it is often necessary to sterilize a container before use. Sterilization by means of radiation, more particularly gamma radiation, has proven its worth in the field of disposable products; however, this radiation is damaging to optical sensors. This particularly affects optical sensors based on porous matrices, such as, for example, fluorescence-based pH sensors. Thus an effective protection system, which can simultaneously be implemented in a cost-effective fashion, is required for such sensors.

WO 02/056023 A1 and DE 100 51 220 A1 have disclosed optical sensors for measuring at least one parameter in a sample. These sensors are based on a device for exciting fluorescence in an analyte-sensitive fluorescent dye, immobilized in a matrix in a sample vessel or reactor, which dye is at least in indirect contact with the sample, and on an evaluation device for the resulting fluorescence response signal. In this case, the analyte concentration can be evaluated or determined by utilizing both the fluorescence decay time and the fluorescence intensity. A disadvantage is the fact that such pH sensor patches, which are based on a hydrophilic carrier matrix, such as e.g. impregnated paper or sol-gel matrices, are damaged, dose-dependent, during radiation sterilization. There is a reduction in both the intensity of the fluorescence of the dye or dyes and also the sensitivity of the sensor patch with respect to the measurement variable.

U.S. Pat. No. 7,390,462 B2 has disclosed a sensor, in which the fluorescent dye is present immobilized in a hydrophilic matrix. In this case, a sensor is claimed with the pH-sensitive fluorescent dye MA-HPDS present in a hydrogel. Here too a disadvantage lies in the fact that such hydrophilic optical sensors are damaged, dose-dependent, during sterilization using gamma radiation. In laboratory technology in particular, such radiation is applied in the case of containers made of polymers. There is a reduction in both the intensity of the fluorescence of the dye or dyes and also the sensitivity of the sensor with respect to the measurement variable. There is particularly severe damage to such a sensor patch if it is in contact with a relatively large volume of air or else with conventional protective gasses such as e.g. nitrogen or argon during the radiation sterilization. The gasses are partly ionized or free radicals are created during the radiation sterilization. During, for example, the sterilization of a gas-filled polymer bag, these radicals react on the walls or else on the sensor surfaces. Sensors based on porous, hydrophilic matrices are particularly susceptible to this because the sensor chemicals must be present immobilized on the surface or inner surface of the matrix due to operating principles so that the sample to be measured can come into contact with the sensor chemicals. The extent of the damage is dependent on, firstly, the radiation dose and, secondly, the ratio of the surface to the volume of the irradiated container containing the sensor patch. This ratio determines the number of ions or radicals that damage the sensor patch or the sensor chemicals contained therein.

DE 10 2009 003 971.6 A1 has disclosed an optical sensor for measuring at least one parameter, which sensor is coated porously with a noble metal layer; this brings about a reaction of reactive particles on the noble metal layer. However, a disadvantage of this is the fact that such a coating is complicated from a technical and mechanical point of view and is connected with high costs; this is something that should be avoided, particularly in the field of disposable products.

The present invention is therefore based on the object of developing a sensor device for an optical sensor, which reduces the sensitivity of the optical sensor towards radiation, more particularly gamma radiation, and which can be implemented in a cost-effective and simple fashion.

SUMMARY OF THE INVENTION

The sensor device according to the invention has at least one optical sensor, a container and a compartmentalization means. The compartmentalization means temporarily divides the container into at least two spaces, wherein the optical sensor is contained in the adjacent space created thus. It is also possible to house two or more sensors in the adjacent space. By way of example, the compartmentalization can be undone after sterilization or a transport procedure.

The term compartmentalization, as used herein, is not restricted in any form and relates to any procedure that is suitable for subdividing a space into at least two spaces. The term compartmentalization means should be considered analogously.

As per a preferred embodiment of the invention, the optical sensor is sterilizable by radiation whilst maintaining the functionality thereof. The sensitivity towards sterilization, for example by means of ionizing radiation, gamma radiation, UV-C, beta or electron radiation, is reduced by means of the compartmentalization means. By reducing the volume of gas in the direct vicinity of the optical sensor, there is an according reduction in the number of reactive particles formed therefrom, which reactive particles have access to the optical sensor and react with the matrix thereof and with the fluorescent dye or fluorescent dyes. This achieves an improved signal-to-noise ratio and a generally higher sensitivity of the optical sensor with respect to the measurement variable thereof. Here the measurement variables can be e.g. the pH value, the dissolved oxygen concentration or other parameters. The compartmentalization or compartmentalization means can be made undone after the radiation sterilization or before the container is used, e.g. as a bioreactor, without breaking the sterile barrier of the container.

As per a further preferred embodiment of the invention, the compartmentalization means makes it possible to delimit the adjacent space from the main space in a gastight fashion. Hence all diffusion of reactive particles is prevented. An evacuation device, which can preferably be regulated in the form of a thermoplastically sealable line or by means of a valve, additionally leads to a reduction in the gas, which reduces the number of reactive particles created during radiation sterilization to a minimum.

In a further preferred embodiment of the invention, the compartmentalization means partly seals the adjacent space with respect to the main space. Free diffusion of the reactive particles created by radiation sterilization is only to be expected in the clear gas space, and so small gaps that connect the two compartments are admissible as a result of the deactivation of the reactive particles in the case of impacts with the walls. Moreover, such an embodiment can be implemented in a simple fashion from the point of view of production technology and in a cost-effective fashion. Here, an evacuation device can remove gas from the entire container and thus furthermore reduce the quantity of reactive particles that are formed.

As per a particularly preferred embodiment of the invention, the compartmentalization means is embodied as a cap covering the optical sensor. The cap can be placed over the sensor or a corresponding device in an accurately fitting fashion and can additionally have a permanent connection to e.g. the sensor frame or the container so as not to constitute an obstruction.

In a further advantageous embodiment of the invention, the compartmentalization means is a tube containing the optical sensor. By way of example, said tube can be placed over the optical sensor while projecting from the container inner wall and thus create a compartmentalization. A plug or corresponding production-technological measures can additionally reduce the internal volume of the tube and thus minimize the number of reactive particles forming in the surroundings of the optical sensor. As a result of an adjacent-space volume reduced in this respect, this likewise reduces the dead space that exists after the isolation from the optical sensor.

According to a further particularly preferred embodiment of the invention, the compartmentalization is carried out by the wall of the container. By way of example, this can be achieved by a clamp, which presses together the wall, or by a pressure closure such as e.g. a ZipLoc® closure. A further option consists of welding or adhesively bonding an easily penetrable material to the place of the compartmentalization or, in the case of a flexible design, welding or adhesively bonding the container to itself. Such embodiments enable a high savings potential and additionally provide secure protection from having too many reactive particles.

As per a further preferred embodiment of the present invention, the adjacent space is a port system that holds the optical sensor. In a further embodiment, this can have one or more holding apparatuses, e.g. destructible plastic rings, that fix the port system. In another embodiment, the port system itself has not been sealed in a gastight fashion but rather is sealed, in a gastight fashion, from the main space by means of a compartmentalization means. The compartmentalization means, for example in the form of a cap or a film, can be broken open or pierced open in the direction of the main space. In order to additionally achieve increased tightness, the port system has at least one seal, for example in the form of O-rings. An evacuation device, which can preferably be regulated in the form of a thermoplastically sealable line or by means of a valve, can additionally lead to a reduction in the gas, which reduces the number of reactive particles created during radiation sterilization to a minimum. The aforementioned embodiment permits the optical sensor element to be radiation sterilized under reduced gas pressure (<1.01325 bar).

As per a particularly preferred embodiment of the invention, the optical sensor determines at least one parameter in a medium. The optical sensor has at least one matrix, which contains at least one fluorescent dye, which is carried by a transparent carrier.

As per a further preferred embodiment of the invention, the optical-sensor matrix is hydrophilic. Particular embodiments can be a sol-gel matrix or a hydrogel, in which the fluorescent dye is present in an immobilized fashion. The hydrophilic property is required for optical sensors in particular, the fluorescent dye of which, embedded in the matrix, must be accessible for an aqueous medium. Optical sensors that have a hydrophilic matrix are naturally very sensitive to sterilization, e.g. by means of gamma radiation. A compartmentalization effectively protects from the influences of reactive particles released by radiation.

As per a further preferred embodiment of the invention, the optical-sensor matrix is porous.

In a further advantageous embodiment of the invention the container made of plastic has at least a partly flexible wall. Such containers in particular, which are predominantly used for single use, require cost-effective and easily producible components, as presented by the present invention.

As per a particularly preferred embodiment of the present invention, the adjacent space is at least partly filled by an aqueous reducing agent. In addition to the protection of the optical sensor from reactive particles as a result of the adjacent space, this also provides protection from direct radiolysis of the sensor chemicals. During radiolysis, for example of the indicator molecules of an optical sensor based on a porous matrix, radical cations are created by the ionizing radiation and these can cause further damage to the sensor chemicals as a result of radical chain reactions. Surprisingly, this damaging effect, which also has a negative influence on the sensor performance, can be largely suppressed by impregnating the sensor matrix with an aqueous reducing agent, such as e.g. 0.1 to thirty-three percent L-ascorbic acid solution. L-ascorbic acid solution, as a radical quencher, effectively suppresses radical chain reactions. Further suitable reducing agents are the salts of L-ascorbic acid, isoascorbic acid, compounds from the class of hydroquinones or glutathione.

FIGS. 1 to 5 show different embodiments of the sensor device.

DETAILED DESCRIPTION OF THE PREFERRED EMBODIMENTS

Figure 1:
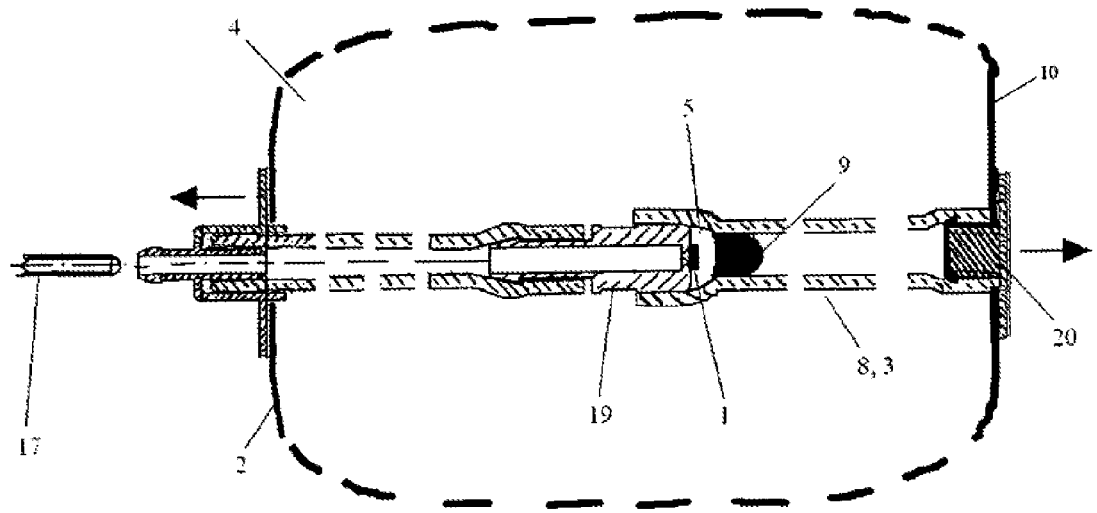
FIG. 1 shows a schematic cross section through an exemplary embodiment of the sensor device, wherein a tube with a plug compartmentalizes the optical sensor with respect to the main space.

As per FIG. 1 to FIG. 4b, the sensor device consists of an optical sensor 1, a container 2 and a compartmentalization means 3. The compartmentalization means 3 temporarily confines the container 2 into a main space 4 and an adjacent space 5, which contains the optical sensor 1. An optical waveguide 17 allows the optical measurement of one or more parameters. It is possible to see that an adjacent space with the smallest possible volume is reached.

Figure 2:
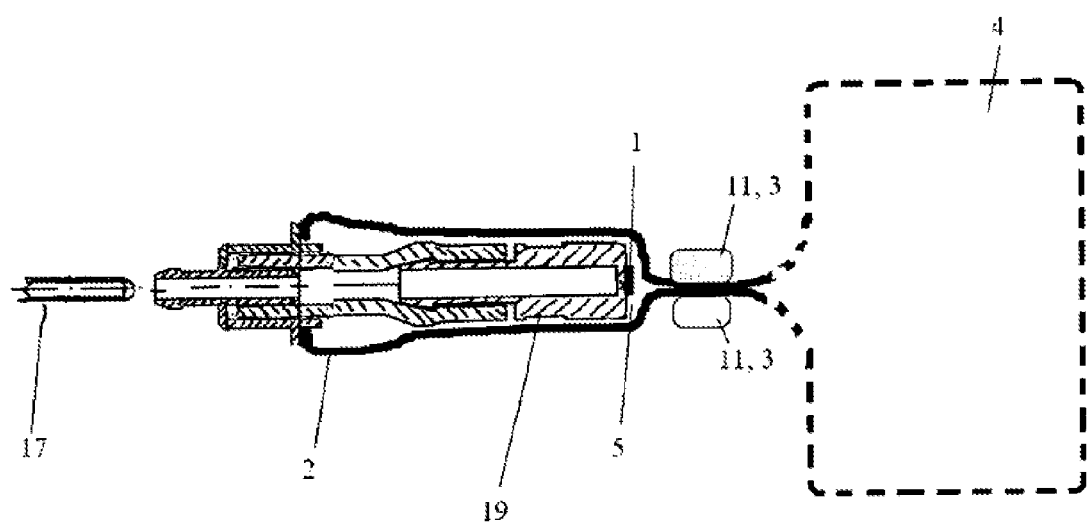
FIG. 2 shows a schematic cross section through an exemplary embodiment of the sensor device, wherein a clamp, as compartmentalization means, compartmentalizes the container into an adjacent space and a main space.
Figure 3:
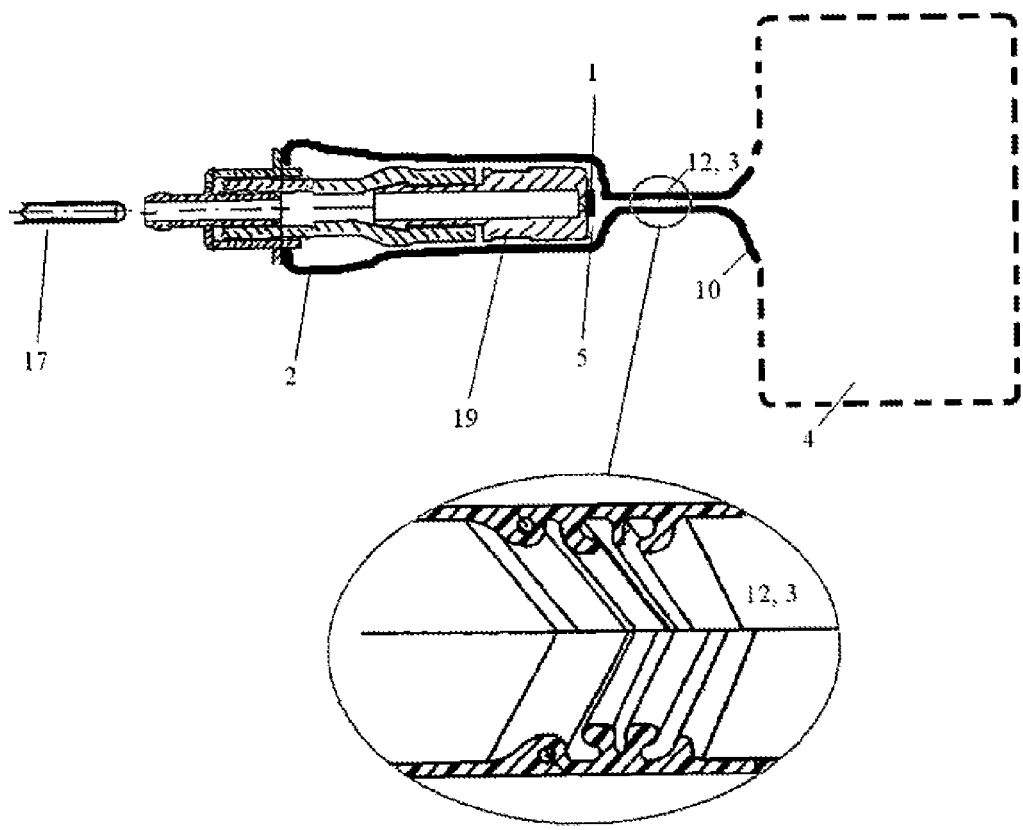
FIG. 3 shows a schematic cross section through an exemplary embodiment of the sensor device, wherein a pressure closure, the cross section of which is illustrated in the enlarged section, compartmentalizes the container into an adjacent space and a main space.

As per FIGS. 1 to 3, the optical sensor 1 is applied to a light-permeable cap 19, for example made of polycarbonate.

FIG. 1 shows a schematic cross section through an exemplary embodiment of the sensor device, wherein a tube 8 or pipe with a plug 9 compartmentalizes the optical sensor 1 with respect to the main space 4. By way of example, the tube 8 can be made from silicone. In place of a plug 9, which can subsequently be plugged into the tube 8, it is also possible to use a tube 8 that already has a reduced gas volume. The tube 8 can, as illustrated here, be seated on a flange 20 or else it can be fixedly welded or adhesively bonded onto the container 2. By pulling thereon and/or on the point of attachment of the optical sensor 1, the tube 8 can be separated from the optical sensor 1 after sterilization, which is illustrated in the direction of the arrow. Conversely, simple compartmentalization is possible before sterilization.

FIG. 2 shows a schematic cross section through an exemplary embodiment of the sensor device, wherein a clamp 11, as compartmentalization means 3, compartmentalizes the container 2 into an adjacent space 5 and a main space 4.

FIG. 3 shows a schematic cross section through an exemplary embodiment of the sensor device, wherein a pressure closure 12, which is illustrated in the enlarged section in a cross section and in an opened state, compartmentalizes the container into an adjacent space 5 and a main space 4. The pressure closure 12 can for example be embodied in the form of a ZipLoc® closure (SC Johnson & Son, Inc., Racine, USA).

Figures 4A, 4B:
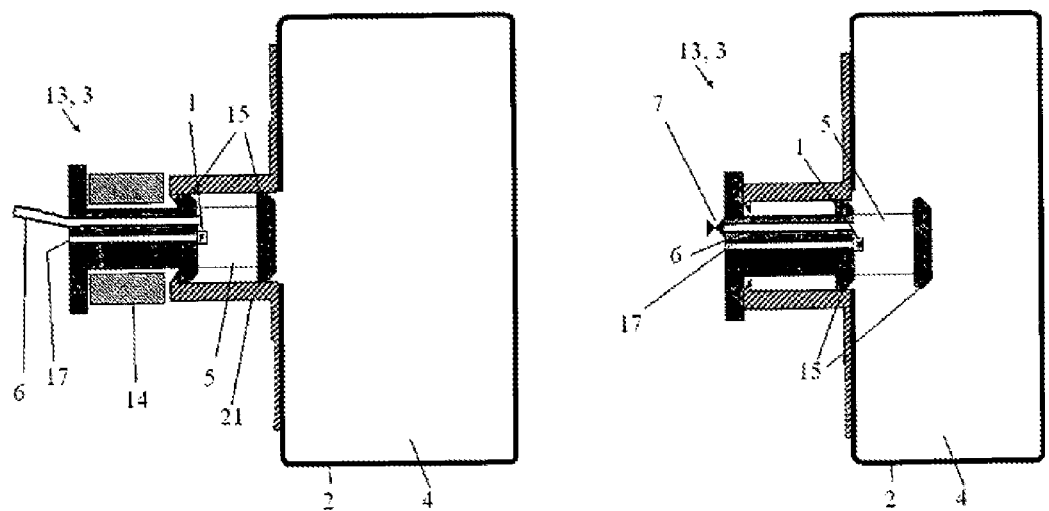
FIG. 4a shows a sectional view through an exemplary embodiment of the sensor device, with a port system, containing the optical sensor, in a compartmentalized state.
FIG. 4b shows a sectional view through an exemplary embodiment of the sensor device, with a port system, containing the optical sensor, in an opened state.

As per FIGS. 4a and 4b, an embodiment of the sensor device consists of a port system 13, which is insulated by seals 15 from the atmosphere and the main space 4. FIG. 4a shows a sectional view through an exemplary embodiment of the sensor device, with a port system 13, containing the optical sensor 1, in a compartmentalized state. Inadvertent opening of the compartmentalization is prevented by means of a holding apparatus 14, for example a plastic ring. The adjacent space 5 can be evacuated via a sealable line 6, as a result of which a lower gas concentration results in a lower number of reactive particles and thus this results in less damage to the optical sensor 1. By way of example, the sealable line 6 can be sealed thermoplastically. FIG. 4b shows a sectional view through an exemplary embodiment of the sensor device with a port system 13 in the opened state and with a valve 7 on the sealable line 6. The seal still situated in the port guidance 21 ensures sterility.

Figure 5:
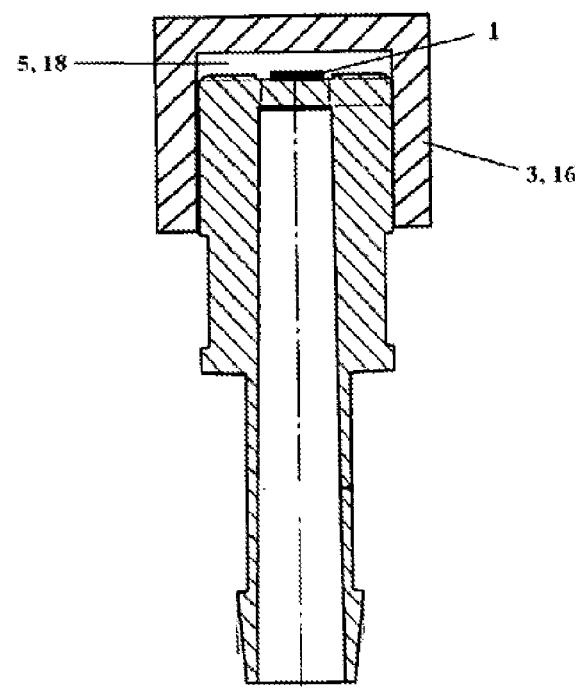
FIG. 5 shows a sectional view through an exemplary embodiment of part of the sensor device with protective cap, containing a reducing agent.

FIG. 5 illustrates a further exemplary embodiment of the sensor device. A cap 16 seals the adjacent space 5 in preferably a gastight and fluid-tight fashion. The adjacent space 5 is filled with an aqueous reducing agent 18 such as e.g. 20% L-ascorbic acid solution. This effectively prevents radiolysis of the sensor chemicals by inhibiting radical chain reactions. Hence the sensor can be radiation sterilized whilst maintaining its sensitivity. Further suitable reducing agents are, for example, the salts of L-ascorbic acid, isoascorbic acid, compounds from the class of hydroquinones or glutathione.

Figure 6:
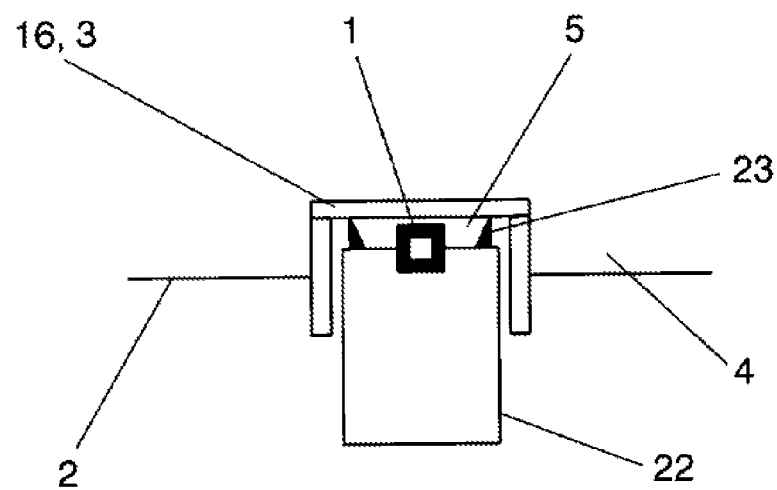
FIG. 6 shows a sectional view through an exemplary embodiment of part of the sensor device with a push-action system in the closed state.
Figure 7:
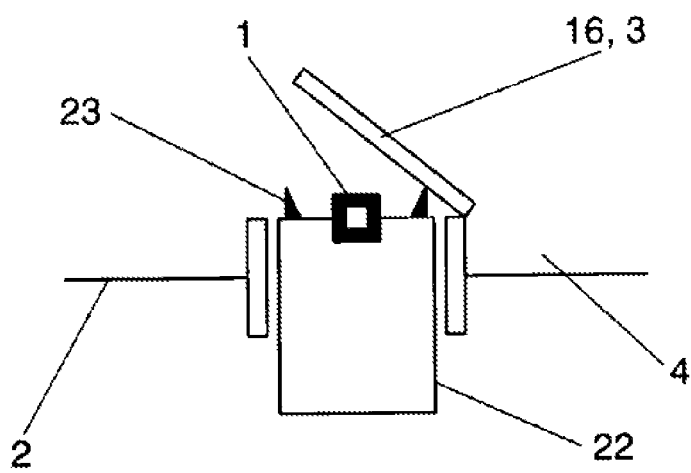
FIG. 7 shows a sectional view through an exemplary embodiment of part of the sensor device with a push-action system in the opened state.

As per FIGS. 6 and 7, a further embodiment of the sensor device consists of a push-action system 22 which pushes open a cap 16 by one or more projections 23. FIG. 6 shows the system in the compartmentalized state; FIG. 7 shows it in the open state. The compartmentalization can be brought about in a complete, a hermetic or only in a partial state. The cap 16 preferably tightly seals the adjacent space 5 from the main space 4 so that there is a spatial volume around the optical sensor 1 that is as small as possible. A vacuum can also be created in the adjacent space 5 by appropriate devices. A predetermined breaking point or other mechanical design features can ease the breaking open or opening. By way of example, the push-action system 22 can be screwed into the main space 4 by a rotational movement and so less force must be applied in order to open the cap 16.

Figure 8:
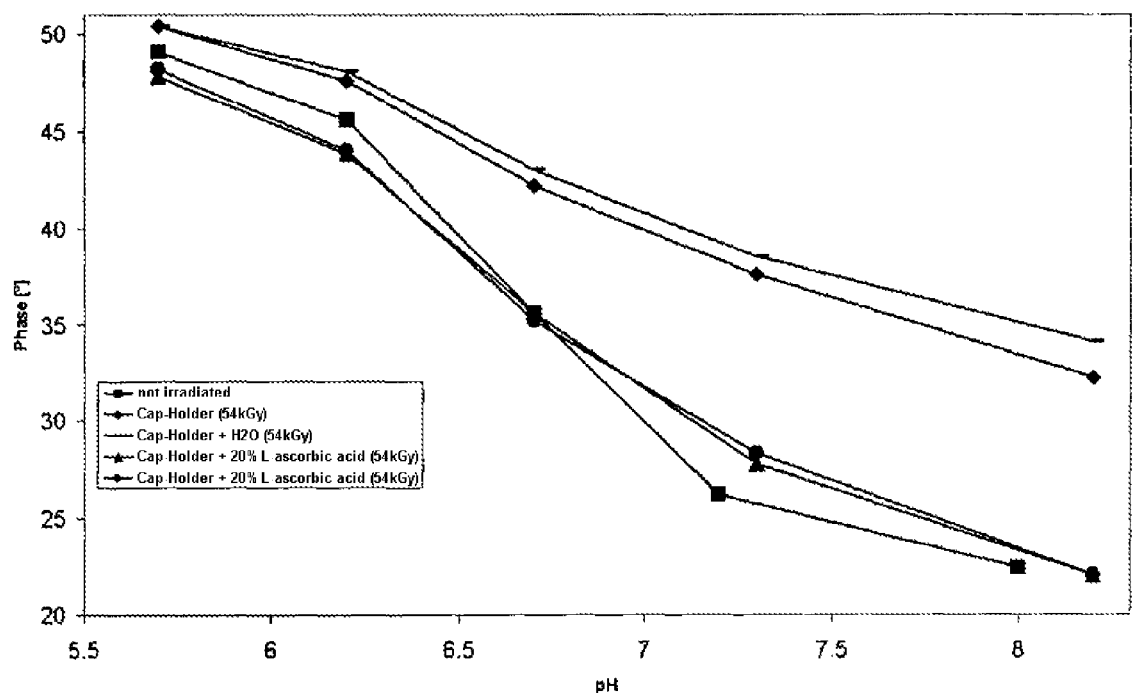
FIG. 8 shows a diagram of the sensitivity of the sensors (pH/phase°).

As per FIG. 8, sensor devices according to the invention are largely very insensitive towards radiation.

An embodiment of the present invention should be explained in more detail using the exemplary embodiment in the following text.

EXAMPLE

A plastic container (Cultibag RM, Sartorius Stedim Biotech GmbH, Göttingen/volume: 10 l) is equipped with four pH sensors (HP8, Presens GmbH, Regensburg) on polycarbonate caps. Two of the polycarbonate caps with the sensor chemicals are covered by a simple protective cap that can be sealed in an airtight fashion; in two further sensor caps, the protective cap is additionally filled with twenty percent L-ascorbic acid solution. The sensors are attached to the wall of the container, with the sensor chemicals facing the center of the container. The device is subsequently filled with 10 l air and tightly sealed. Thereupon there is gamma irradiation at 56.0 kGy (Co60 source, Beta-Gamma-Service GmbH & Co. K G, Wiehl). After the irradiation, the sensors are taken from the containers and measured with a transmitter (pH-1 mini, Presens GmbH, Regensburg) in buffers with pH values between 5.7 and 8.5. The sensitivity and hence the quality of the sensors corresponds to the difference in the phases at pH 6.0 and pH 8.0 (see FIG. 8).

The sensors that were treated by the reducing agent have a similar characteristic to the non-irradiated sensor. This corresponds to largely being very insensitive towards the irradiation.

The invention claimed is:

1. A sterilizable container (2) comprising:
a wall (10) defining an interior of the container (2);
an optical sensor (1) in the interior of the container (2); and
a compartmentalization means (3) for dividing the interior of the container (2) into an adjacent space (5) that contains the optical sensor (1) and a main space (4) that is divided from the adjacent space (5) during sterilization of the main space (4) by radiation and for selectively placing the main space (4) in communication with the adjacent space (5) and the optical sensor (1) upon completion of the sterilization by radiation.

2. The sterilizable container of claim 1, wherein the compartmentalization means (3) is configured to delimit the adjacent space (5) from the main space (4) in a gastight fashion.

3. The sterilzable container of claim 1, wherein the adjacent space (5) can be evacuated.

4. The sterilizable container of claim 1, wherein the compartmentalization means (3) partly seals the adjacent space (5) with respect to the main space (4).

5. The sterilizable container of claim 1, wherein the compartmentalization means is a pressure closure (12).

6. The sterilizable container of claim 1, wherein the container (2) is made of plastic and has at least a partly flexible wall (10).

7. The sterilizable container of claim 1, wherein the adjacent space (5) is at least partly filled by an aqueous reducing agent (18).

8. The sterilizable container (2) of claim 1, wherein the wall (10) of the container (2) is flexible, and wherein the compartmentalization means (3) comprises a part in the interior of the container (2) that closes around the optical sensor (1) in a first flexed condition of the wall (10) to form the adjacent space (5) and that opens the optical sensor (1) to the main space (4) in a second flexed condition of the wall (10).

9. The sterilizable container (2) of claim 8, wherein the compartmentalization means (3) further comprises a tube or cover that closes around the optical sensor (1) in the first flexed condition of the wall (10) to form the adjacent space (5) and that separates from the optical sensor (1) in the second flexed condition of the wall (10) to open the optical sensor (1) to the main space (4).

10. The sterilizable container (2) of claim 8, wherein the compartmentalization means (3) further comprises two spaced apart sections of the wall (10) that close onto one another in the first flexed condition of the wall (10) to form the adjacent space (5) that contains the optical sensor (1).

11. The sterilizable container of claim 10, wherein the compartmentalization means (3) comprises a clamp (11) that presses together the two wall sections of the wall (10).

12. The sterilizable container (2) of claim 1, further comprising a port (21) projecting from the wall (10), the optical sensor (1) being disposed in the port (21), the compartmentalization means (3) comprises a seal (15) engaged in the port (21) so that the adjacent space (5) is on a side of the seal (15) in the port (21) and so that the main space (4) is defined in the container (2) on a side of the seal (15) opposite the optical sensor (1), the seal (15) being selectively displaceable from the port (21) for placing the adjacent space (5) and the optical sensor (1) therein in communication with the main space (4) upon completion of the sterilization by radiation.

* * * * *